United States Patent

Eller et al.

[11] Patent Number: 6,111,141
[45] Date of Patent: Aug. 29, 2000

[54] PREPARATION OF N-ETHYLDIISOPROPYLAMINE

[75] Inventors: Karsten Eller, Ludwigshafen; Bernd Fiege, Frankenthal; Andreas Henne, Neustadt; Heinz-Josef Kneuper, Niederkirchen, all of Germany

[73] Assignee: BASF Aktiengesellschaft, Ludwigshafen, Germany

[21] Appl. No.: 09/474,828

[22] Filed: Dec. 30, 1999

[30] Foreign Application Priority Data

Jan. 14, 1999 [DE] Germany .............. 199 01 135

[51] Int. Cl.⁷ ............................................. C07C 209/26
[52] U.S. Cl. ......................................................... 564/473
[58] Field of Search ............................................ 564/473

[56] References Cited

U.S. PATENT DOCUMENTS 2,692,285  10/1954  Robinson et al. .
4,404,404   9/1983  Swift et al. .................. 564/473

FOREIGN PATENT DOCUMENTS 02 180 854  7/1990  Japan .

OTHER PUBLICATIONS

Hunig und Kiessel, 91, 380–392 (1958), Spezifische Protonenacceptoren als . . .
Autonomic Blocking AGents . . . , 1911–1920, Robinson, 1951.
Chem. Reaction Eng. 2nd Ed., 164–168, John Wiley, 1972.

*Primary Examiner*—Johann Richter
*Assistant Examiner*—Brian J. Davis
*Attorney, Agent, or Firm*—Keil & Weinkauf

[57] ABSTRACT

In the process for preparing N-ethyldiisopropylamine by reacting acetaldehyde with diisopropylamine and hydrogen at elevated temperature and under pressure in the presence of a hydrogenation catalyst, the catalyst comprises an oxidic support material selected from the group consisting of zirconium dioxide, titanium dioxide, aluminum oxide, silicon dioxide, zinc oxide, magnesium oxide, cerium dioxide, clays and zeolites or mixtures thereof.

9 Claims, No Drawings

PREPARATION OF N-ETHYLDIISOPROPYLAMINE

The present invention relates to a process for preparing N-ethyldiisopropylamine (Hünig base) of the formula

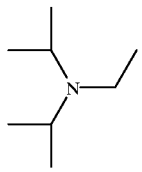

by reacting acetaldehyde with diisopropylamine and hydrogen at elevated temperature and under pressure in the presence of a hydrogenation catalyst.

N-ethyldiisopropylamine is an important amine, which is used as a strong base of low nucleophilicity in elimination reactions and as a catalyst or auxiliary base in the organic synthesis of, for example, active compounds (see WO 98/07430).

Chem. Ber. 91, (1958) 380–92 describes the synthesis of N-ethyldiisopropylamine by reacting diisopropylamine with diethyl sulfate. In this case, sulfates arise as unwanted by-products which must then be disposed of in a costly manner.

The reaction of diisopropylamine with ethyl iodide described in J. Org. Chem. 16, (1951) 1911–20 and U.S. Pat. No. 2,692,285 for the synthesis of N-ethyldiisopropylamine also leads to unwanted salts as by-products.

JP-A-02 180 854 discloses a batchwise process for preparing N-ethyldiisopropylamine by reductive dialkylation of ethylamine with acetone in the presence of a noble metal catalyst. The low yields are a disadvantage of this process.

JP-A-02 180 854 further discloses a batchwise process for preparing N-ethyldiisopropylamine by reacting diisopropylamine with acetaldehyde and hydrogen in the presence of a noble metal catalyst, such as Pd/C, Ru/C, Rh/C and Pt/C, where the reaction is carried out in an autoclave in such a manner that the acetaldehyde is fed gradually during the reaction of the reaction mixture (cf. loc. cit.: claim 2 and Examples Nos. 5 and 6) to achieve good yields.

According to JP-A-02 180 854, the yields of N-ethyldiisopropylamine in the reaction of diisopropylamine with acetaldehyde and hydrogen are poor (less than 10%), if the diisopropylamine and the acetaldehyde are charged into the autoclave together from the start (loc. cit.: Comparative Example 1).

The low space-time yields owing to the batchwise procedure are disadvantages of this process.

A continuous procedure for preparing N-ethyldiisopropylamine would, according to JP-A-02 180 854, require the catalytic reaction of acetaldehyde with diisopropylamine and hydrogen to be carried out in a complex manner in a reactor cascade, e.g. a stirred-tank cascade, with some of the acetaldehyde to be reacted being fed to each reactor of the cascade, or a tube reactor having a plurality of feed points for the acetaldehyde along the reactor, e.g. a compartment reactor having a plurality of feed points, as taught, for example, in general terms for similar cases in O. Levenspiel, 'Chemical Reaction Engineering', $2^{nd}$ Ed., (1972) pages 164–168, in particular 166–167, John Wiley.

It is an object of the present invention, therefore, to discover an improved, non-complex, economical process which can be carried out batchwise and especially continuously for preparing N-ethyldiisopropylamine with good space-time yields.

We have found that this object is achieved by a process for preparing N-ethyldiisopropylamine by reacting acetaldehyde with diisopropylamine and hydrogen at elevated temperature and under pressure in the presence of a hydrogenation catalyst which comprises the catalyst comprising an oxidic support material selected from the group consisting of zirconium dioxide, titanium dioxide, aluminum oxide, silicon dioxide, zinc oxide, magnesium oxide, cerium dioxide, clays and zeolites or mixtures thereof.

Generally, in the process of the invention, the catalysts are preferably used in the form of catalysts which only consist of catalytically active mass and possibly a forming aid (e.g. graphite or stearic acid) if the catalyst is used as a shaped body, that is contain no other catalytically inactive accompanying materials.

In this context, the oxidic supporting materials zirconium dioxide ($ZrO_2$), titanium dioxide ($TiO_2$), aluminum oxide ($Al_2O_3$), silicon dioxide ($SiO_2$), zinc oxide (ZnO), magnesium oxide (MgO), cerium dioxide ($CeO_2$), clays and zeolites are considered to belong to the catalytically active mass.

The catalysts are used in such a manner that the catalytically active mass ground to powder is introduced into the reaction vessel or, preferably, that the catalytically active mass, after grinding, mixing with forming aids, forming and heating/cooling are disposed in the reactor as shaped catalyst bodies, for example as pellets, balls, rings, extrudates (e.g. rods).

The concentration figures (in % by weight) of the catalyst components are based in each case—unless stated otherwise—on the catalytically active mass of the finished catalyst after its final heat treatment and before its reduction with hydrogen.

The catalytically active mass of the catalyst after its final heat treatment and before its reduction with hydrogen is defined as the sum of the masses of the catalytically active constituents and the abovementioned catalyst support materials and essentially comprises the constituents zirconium dioxide ($ZrO_2$), titanium dioxide ($TiO_2$), aluminum oxide ($Al_2O_3$), silicon dioxide ($SiO_2$), zinc oxide (ZnO), magnesium oxide (MgO), cerium dioxide ($CeO_2$), clays, zeolites or mixtures of two or more of these components and one or more metals or their oxides selected from the group consisting of Cr, Mo, W, Re, Ru, Rh, Pd, Os, Ir, Pt, Ag, Au, Fe, Co, Ni and Cu.

The sum of the abovementioned essential constituents of the catalytically active mass, with the components Cr, Mo, W, Re, Ru, Rh, Pd, Os, Ir, Pt, Ag, Au, Fe, Co, Ni and/or Cu being calculated as metal in the oxidation state 0, is customarily from 70 to 100% by weight, preferably from 80 to 100% by weight.

The catalytically active mass of the catalysts used in the process of the invention can further comprise one or more elements (oxidation state 0) or their inorganic or organic compounds selected from the groups consisting of I A, II A, III A, IV A, V A, VI A, I B, II B, III B, IV B and V B of the Periodic Table.

Examples of such elements or their compounds are:

Transition metals, such as Mn or $Mn_2O_3$; lanthanides, such as Pr or $Pr_2O_3$; alkali metal oxides, such as $Na_2O$; alkali metal carbonates; alkaline earth metal oxides, such as CaO; alkaline earth metal carbonates, such as $CaCO_3$; boron oxide ($B_2O_3$); niobium oxalate; vanadyl pyrophosphate.

The catalytically active mass of the catalysts used in the process of the invention generally comprises after their final heat treatment and before their reduction with hydrogen from 50 to 99.9% by weight, preferably from 60 to 99.9% by weight, particularly preferably from 80 to 99.9% by weight, of $ZrO_2$ and/or $TiO_2$ and/or $Al_2O_3$ and/or $SiO_2$ and/or ZnO and/or MgO and/or $CeO_2$ and/or clays and/or zeolites, from 0.1 to 50% by weight, preferably from 0.1 to 40% by weight, particularly preferably from 0.1 to 20% by weight, very particularly preferably from 0.1 to 5% by weight, of Cr, Mo, W, Re, Ru, Rh, Pd, Os, Ir, Pt, Ag, Au, Fe, Co, Ni and/or Cu, calculated as metal in the oxidation state 0, and from 0 to 30% by weight, preferably from 0 to 25% by weight, particularly preferably from 0 to 20% by weight, of one or more elements (oxidation state 0) or their inorganic or organic compounds selected from the groups I A, II A, III A, IV A, V A, VI A, I B, II B, III B, IV B and V B of the Periodic Table.

Preferred catalysts comprise in their catalytically active mass from 50 to 99.9% by weight of $ZrO_2$ and/or $TiO_2$ and/or $Al_2O_3$ and/or $SiO_2$ and/or MgO, particularly preferably from 60 to 99.9% by weight of $ZrO_2$ and/or $Al_2O_3$ and/or $SiO_2$ and/or MgO, very particularly preferably from 60 to 99.9% by weight of $ZrO_2$.

Preferred catalysts comprise in their catalytically active mass from 0.1 to 20% by weight, in particular from 0.1 to 5% by weight, of Re, Pd, Pt, Ru, Os, Rh, Ir, Ag and/or Au, calculated as metal in the oxidation state 0.

More preferred catalysts comprise in their catalytically active mass from 0.1 to 5% by weight of Pd and/or Pt and/or Ag and/or Ru, particularly preferably from 0.1 to 5% by weight of Pd and/or Pt, very particularly preferably from 0.1 to 1.3% by weight of Pd and from 0.1 to 1.3% by weight of Pt, where the noble metal contents are calculated in each case as metal in the oxidation state 0.

Various processes are possible for preparing the catalysts used in the process of the invention. They are obtainable, for example, by peptizing pulverulent mixtures of the hydroxides, carbonates, oxides and/or other salts of the catalyst components with water and subsequent extruding and heating/cooling of the resultant mass.

Precipitation methods can be used for preparing the catalysts used in the process of the invention. Thus, they can be obtained, for example, by a joint precipitation of the metal components from an aqueous salt solution containing these metals by using mineral bases in the presence of slurry or suspension of fine-grained powder of the sparingly soluble catalyst support material, e.g. a sparingly soluble oxygen compound of aluminum, titanium, silicon and/or zirconium, and subsequent washing, drying and calcination of the resulting precipitate. Sparingly soluble oxygen compounds of aluminum, titanium, silicon and/or zirconium which can be used are, for example, aluminum oxide, titanium dioxide, zirconium dioxide, zirconium oxide hydrate and silicon dioxide which are advantageously obtained as a slurry by precipitating the sparingly soluble compounds of aluminum, titanium, silicon and/or zirconium from the corresponding aqueous salt solutions using mineral bases.

Advantageously, the catalysts used in the process of the invention are prepared via a joint precipitation (mixed precipitation) of all of their components. For this purpose, expediently, an aqueous salt solution comprising the catalyst components is admixed in the warm and with stirring with an aqueous mineral base, in particular an alkali metal base, for example sodium carbonate, sodium hydroxide, potassium carbonate or potassium hydroxide, until the precipitation is complete. The type of salts used is generally not critical: since in this procedure the water solubility of the salts is principally relevant, one criterion is their high water solubility required for preparing these relatively highly concentrated salt solutions. It is considered obvious that in the selection of the salts of the individual components, clearly, only salts are selected which have those anions which do not lead to interferences such as giving rise to unwanted precipitations or, due to complexing, making the precipitation more difficult or preventing it.

The precipitates obtained in these precipitation reactions are generally not chemically homogeneous and consist, inter alia, of mixtures of the oxides, oxide hydrates, hydroxides, carbonates and insoluble and basic salts of the metals used. It can prove expedient for the filterability of the precipitates if they are aged, i.e. if they are allowed to stand for some further time after the precipitation, optionally in the presence of heat or with the passage of air.

The precipitates obtained by these precipitation processes are further processed as customary to give the catalysts of the invention. After the washing step, they are generally dried at from 80 to 200° C., preferably at from 100 to 150° C., and then calcined. The calcination is generally carried out at temperatures from 300 to 800° C., preferably from 400 to 600° C., in particular from 450 to 550° C.

After the calcination, the catalyst is expediently conditioned, that is, either it is set to a defined particle size by grinding or, after it is ground, it is mixed with forming aids such as graphite or stearic acid, compressed by a press to give moldings, e.g. pellets, and heat-treated. The heat-treatment temperatures generally correspond here to the temperatures during calcination.

The catalysts prepared in this manner comprise the catalytically active metals in the form of a mixture of their oxygen compounds, i.e. in particular as oxides and mixed oxides.

Preferably, the catalysts used in the process of the invention are prepared by impregnation of zirconium dioxide ($ZrO_2$), titanium dioxide ($TiO_2$), aluminum oxide ($Al_2O_3$), silicon dioxide ($SiO_2$), zinc oxide (ZnO), magnesium oxide (MgO), cerium dioxide ($CeO_2$), clays or zeolites or mixtures of two or more of these support materials which are present, for example, in the form of powder or shaped bodies, such as rods, pellets, balls or rings.

Aluminum oxide can be used in various modifications, preference is given to $\alpha$-, $\gamma$- or $\theta$-$Al_2O_3$.

Zirconium dioxide is preferably used in the monoclinic or tetragonal form, very particularly preferably in the monoclinic form, and titanium dioxide is preferably used as anatase or rutile.

Silicon dioxide can be obtained and used, for example, via a precipitation from water glass or via the sol-gel process, or used as mesoporic $SiO_2$, e.g. as mesoporic $SiO_2$ having a specific surface area of the mesopores of at least 500 m$^2$/g and a pore volume of the mesopores of at least 1.0 ml/g according to DE-A-196 39 016, or used as silica gel (e.g. as in Ullmann, Enzykl. Techn. Chem., [Ullmanns Encyclopaedia of Industrial Chemistry], 4th Edition, Vol. 21, (1982) pp. 457–63) or in the form of silicates, such as aluminosilicates (e.g. as in Nature, Volume 359, (1992), p. 710–12), magnesium silicates (e.g. steatite), zirconium silicates, cerium silicates or calcium silicates.

Clays suitable as support materials consist predominantly of phyllosilicates and/or sheet silicates. Those which are highly suitable are, for example, montmorillonite, kaolin or hectorite.

Suitable zeolitic support materials are alkali metal aluminosilicates or alkali earth metal aluminosilicates, e.g. of the formula $M_{2/z}O \cdot Al_2O_3 \cdot xSiO_2 \cdot yH_2O$, where M is a monovalent or divalent metal, H, [NH$_4$], z is the valency, x=from 1.8 to approximately 12 and y=from 0 to approximately 8. Those which are highly suitable are, for example, faujasite or pentasile.

The shaped bodies of the abovementioned oxidic support materials can be prepared by the customary processes.

These oxidic support materials are likewise impregnated by the customary processes, such as described in EP-A-599 180, EP-A-673 918 or A. B. Stiles, Catalyst Manufacture—Laboratory and Commercial Preparations, Marcel Dekker, New York (1983), by applying a corresponding metal salt solution in each case in one or more impregnation stages, the metal salts used being, for example, corresponding nitrates, acetates or chlorides. The mass is dried after the impregnation and, if appropriate, calcined.

The impregnation can be carried out by what is termed the incipient wetness method, in which the oxidic support material is maximally moistened up to saturation with the impregnation solution in accordance with its water absorption capacity. However, the impregnation can also be carried out in a supernatant solution.

In the case of multistage impregnation processes, it is expedient to carry out drying and, if appropriate, calcination between individual impregnation steps. The multistage impregnation is advantageously employed especially when the oxidic support material is to be charged with a relatively large amount of metal.

To apply a plurality of metal components onto the oxidic support material, the impregnation can be carried out simultaneously with all metal salts or in any desired sequence of the individual metal salts in succession.

The catalyst used in the process of the invention can be reduced prior to its use. The reduction can be carried out at atmospheric pressure or under pressure. If reduction is performed at atmospheric pressure, a procedure is followed such that the catalyst is heated under an inert gas, for example nitrogen, up to the reduction temperature and the inert gas is then slowly replaced by hydrogen.

In the case of a reduction under pressure, practically a procedure is followed such that the reduction is also performed at the pressures and temperatures later also employed in the hydrogenation reaction. The reduction time must be selected as a function of temperature and hydrogen pressure, i.e. the more drastic the conditions, the shorter a reduction time can be selected.

Generally, reduction is carried out at from 80 to 250° C., a hydrogen pressure from 0.5 to 350 bar and a time from 1 to 48 h.

However, it is equally possible to use the unreduced catalyst in the process of the invention. In this case, the catalyst is then reduced simultaneously under the process conditions. After a short operating time of the process of the invention of a few hours or a few days, the reduction of the catalyst is usually virtually complete.

The catalyst can be completely or partially reduced separately from the amination reactor in a suitable apparatus or directly prior to the start of the amination in the amination reactor.

The process of the invention may be carried out as follows:

The process of the invention may be carried out batchwise or particularly preferably continuously, with the catalyst preferably being disposed as a fixed bed in the reactor.

The process can be carried out in the liquid phase or in the gas phase. Preference is given to the fixed-bed process in the liquid phase. Depending on the reaction conditions chosen (pressure, temperature), however, a certain proportion of the starting materials will always be present in the gaseous state in accordance with the partial pressure.

The two starting materials diisopropylamine and acetaldehyde can be used in a stoichiometric, superstoichiometric or substoichiometric molar ratio. The molar ratio of diisopropylamine to acetaldehyde is generally from 0.5 to 10 mol/mol.

If the process is carried out in the presence of a solvent, the molar ratio of diisopropylamine to acetaldehyde is generally from 0.6 to 2, preferably from 0.7 to 1.5, particularly preferably from 0.9 to 1.2, very particularly preferably from 1.0 to 1.2, mol/mol.

If the process is carried out in the absence of a solvent, the molar ratio of diisopropylamine to acetaldehyde is generally from 1 to 5, preferably from 1.2 to 4.0, particularly preferably from 1.3 to 3.5 mol/mol.

The two starting materials diisopropylamine and acetaldehyde are used in pure form, i.e. undiluted, or as a solution in an inert solvent in the process of the invention.

Preferred solvents are water, alcohols such as methanol and ethanol, ethers, such as THF, and amides such as DMAC, DMF and NMP. Particularly preferred solvents are water, ethanol and NMP. The solutions are generally used at a concentration of from 5 to 80% by weight, preferably from 20 to 70% by weight.

The hydrogen is generally fed to the reaction in a large molar excess based on the acetaldehyde. Usually, the maximum throughput of the gas circulation pump is employed. Typical ranges are from 0.5 to 15, preferably from 1 to 5, m$^3$ (S.T.P)/l$_{cat}$/h (m$^3$ (S.T.P)=gas volume converted to standard conditions). The actual water consumption is followed via the pressure regulator.

In the case of the preferred continuous procedure of the process in a fixed-bed reactor, e.g. tube reactor, the space velocity is usually from 0,03 to 1,5 kg$_{acetaldehyde}$l$_{cat.}^{-1}$h$^{-1}$, preferably from 0,05 to 1,0 kg$_{acetaldehyde}$l$_{cat.}^{-1}$h$^{-1}$, with any solvent present not being taken into account for calculating the space velocity. The catalyst space velocity figures are therefore based on the acetaldehyde, calculated as 100%, regardless of whether this is used in solution or in pure form. The catalyst volume figures are based on the bulk volume.

The reaction temperature depends on the catalyst activity, the amount of solvent and on the chosen space velocity of the catalyst. Suitable reaction temperatures are generally from 80 to 250° C., preferably from 100 to 180° C., particularly preferably from 110 to 170° C.

The process of the invention is generally carried out at a pressure of from 5 to 350 bar, preferably from 50 to 250 bar, which is established by the appropriate compression of hydrogen.

After passage through the reactor, preferably, some of the discharge, after its passage through a heat exchanger, is recycled to the reactor (liquid recirculation), in order to dissipate the heat of reaction. The amount recycled per unit time is a function of the catalyst space velocity and the reactor size. It is generally from 1 to 20 times the amount of the feed. Preferably, the amount recycled per unit time is set to be as high as possible, i.e. at the maximum throughput rate of the recirculation pump.

The work-up of the reaction discharge and isolation of the process product can be carried out by the customary methods, e.g. by fractional continuous or batchwise distillation or rectification. Rectification can be carried out, for example, at atmospheric pressure or a slight underpressure or overpressure, at reflux ratios of from 1:1 to 10:1 and in towers having from 5 to 60 theoretical plates.

If a solvent is used in the process, this can (with the exception of water as solvent) be recovered during the distillation and recycled to the reaction.

If a molar excess of diisopropylamine, based on acetaldehyde, is used in the process, the recovery of the amine and subsequent recirculation to the synthesis is particularly economic.

EXAMPLES

Example 1

Into an electrically heated tube reactor were installed 800 ml of a catalyst which consisted of 1% of Pd on 19% of MgO and 80% of $Al_2O_3$ in rod form. The catalyst was reduced at atmospheric pressure at 200° C. At 100° C. and 200 bar hydrogen pressure, 87 g of diisopropylamine and 48 g of acetaldehyde (molar ratio amine/aldehyde=0.8) were passed over the catalyst (space velocity: 0.06 $kg_{acetaldehyde} l_{cat.}^{-1} h^{-1}$) per hour in the bottom-phase procedure. The amount recycled was 2 l h$^{-1}$. With quantitative acetaldehyde conversion, the selectivity for the Hünig-base was 46.9 mol %.

Example 2

Into an electrically heated tube reactor were installed 800 ml of a catalyst which consisted of 0.9% of Pd and 0.1% of Pt on $ZrO_2$ in rod form. The catalyst was reduced at atmospheric pressure at 140° C. At 120° C. and 200 bar hydrogen pressure, 90 g of diisopropylamine and 50 g of acetaldehyde (molar ratio amine/aldehyde=0.8) were passed over the catalyst (space velocity: 0.06 $kg_{acetaldehyde} l_{cat.}^{-1} h^{-1}$) per hour in the bottom-phase procedure. The amount recycled was 3 l h$^{-1}$. With quantitative acetaldehyde conversion, the selectivity for the Hünig-base was 71.3 mol %.

After 7 days, the feed was changed to 181 g of diisopropylamine and 78 g of acetaldehyde (molar ratio of amine/aldehyde=1.0) (space velocity: 0.10 $kg_{acetaldehyde} l_{cat.}^{-1} h^{-1}$). With quantitative acetaldehyde conversion, the selectivity to the Hünig base was 68.3 mol %.

After 18 days, the feed mixture was changed over to 361 g of diisopropylamine and 100 g of acetaldehyde per hour (molar ratio amine/aldehyde=1.6) (space velocity: 0.13 $kg_{acetaldehyde} l_{cat.}^{-1} h^{-1}$). With quantitative acetaldehyde conversion, the selectivity to the Hünig base was 65.6 mol %.

Example 3

Into an electrically heated tube reactor were installed 800 ml of a catalyst which consisted of 0.5% of Pd on $\alpha$-$Al_2O_3$ in rod form. The catalyst was reduced at atmospheric pressure at 140° C. At 120° C. and 200 bar hydrogen pressure, 181 g of diisopropylamine and 50 g of acetaldehyde (molar ratio amine/aldehyde=1.6) were passed over the catalyst (space velocity: 0.06 $kg_{acetaldehyde} l_{cat.}^{-1} h^{-1}$) per hour in the bottom-phase procedure. The amount recycled was 3 l h$^{-1}$. With quantitative acetaldehyde conversion, the selectivity for the Hünig-base was 62.7 mol %.

After 4 days, the feed was changed to 361 g of diisopropylamine and 100 g of acetaldehyde (molar ratio of amine/aldehyde=1.6) per hour (space velocity: 0.13 $kg_{acetaldehyde} l_{cat.}^{-1} h^{-1}$). With quantitative acetaldehyde conversion, the selectivity for the Hünig base was 49.7 mol %.

Example 4

Into an electrically heated tube reactor were installed 800 ml of a catalyst which consisted of 0.3% of Pd, 4.6% of Ag and 1% of $Mn_2O_3$ on $SiO_2$ in rod form. The catalyst was reduced at 200 bar and 140° C. At 140° C. and 200 bar hydrogen pressure, 229.5 g of diisopropylamine, 98 g of acetaldehyde (molar ratio of amine/aldehyde=1.0) and 153 g of ethanol as solvent were passed over the catalyst per hour in the bottom-phase procedure (space velocity: 0.12 $kg_{acetaldehyde} l_{cat.}^{-1} h^{-1}$). The amount recycled was 3 l h$^{-1}$. With quantitative acetaldehyde conversion, the selectivity for the Hünig base was 55.1 mol %.

After 26 days the feed was changed over to 101.1 g of diisopropylamine, 50 g of acetaldehyde (molar ratio of amine/aldehyde=1.0) and 50 g of water as solvent per hour (space velocity: 0.06 $kg_{acetaldehyde} l_{cat.}^{-1} h^{-1}$). With quantitative acetaldehyde conversion, the selectivity for the Hünig base was 45.6 mol %.

After 33 days the feed was changed over to 166.1 g of diisopropylamine and 50 g of acetaldehyde (molar ratio of amine/aldehyde=1.5) per hour (space velocity: 0.06 $kg_{acetaldehyde} l_{cat.}^{-1} h^{-1}$). With quantitative acetaldehyde conversion, the selectivity for the Hünig base was 46.2 mol %.

After 37 days the feed was changed over to 332.1 g of diisopropylamine and 50 g of acetaldehyde (molar ratio of amine/aldehyde=3.0) per hour (space velocity: 0.06 $kg_{acetaldehyde} l_{cat.}^{-1} h^{-1}$). With quantitative acetaldehyde conversion, the selectivity for the Hünig base was 49.4 mol %.

Example 5

Into an electrically heated tube reactor were installed 800 ml of a catalyst which consisted of 0.5% of Pd on $\gamma$-$Al_2O_3$ in rod form. The catalyst was reduced at atmospheric pressure at 140° C. At 120° C. and 200 bar hydrogen pressure, 181 g of diisopropylamine and 50 g of acetaldehyde (molar ratio amine/aldehyde=1.6) were passed over the catalyst (space velocity: 0.06 $kg_{acetaldehyde} l_{cat.}^{-1} h^{-1}$) per hour in the bottom-phase procedure. The amount recycled was 3 l h$^{-1}$. With quantitative acetaldehyde conversion, the selectivity for the Hünig-base was 76.3 mol %.

After 16 days, the feed was changed over to 361 g of diisopropylamine and 100 g of acetaldehyde (molar ratio of amine/aldehyde=1.6) per hour (space velocity: 0.13 $kg_{acetaldehyde} l_{cat.}^{-1} h^{-1}$) and the temperature was increased to 140° C. With quantitative acetaldehyde conversion, the selectivity for the Hünig base was 64.5 mol %.

Example 6

Into an electrically heated tube reactor were installed 800 ml of a catalyst which consisted of 0.4% of Pt and 0.4% of Pd on $ZrO_2$ in pellet form. The catalyst was reduced at atmospheric pressure at 140° C. At 130° C. and 200 bar hydrogen pressure, 86.6 g of diisopropylamine and 48 g of acetaldehyde (molar ratio amine/aldehyde=0.8) were passed over the catalyst (space velocity: 0.06 $kg_{acetaldehyde} l_{cat.}^{-1} h^{-1}$) per hour in the bottom-phase procedure. The amount recycled was 6 l h$^{-1}$. With quantitative acetaldehyde conversion, the selectivity for the Hünig-base was 66.7 mol %.

Example 7

In a similar manner to Example 6, at 120° C., 216.6 g of diisopropylamine and 96 g of acetaldehyde (molar ratio of amine/aldehyde=1.0) were passed over the catalyst per hour in the bottom-phase procedure (space velocity: 0.12 $kg_{acetaldehyde}l_{cat.}^{-1}h^{-1}$). The amount recycled was 3 l h$^{-1}$. With quantitative acetaldehyde conversion, the selectivity for the Hünig base was 53.5 mol %.

After 42 days, the temperature was increased to 130° C. and the feed was changed over to 222 g of diisopropylamine, 98 g of acetaldehyde (molar ratio of amine/aldehyde=1.0) and 55.5 g of ethanol as solvent per hour (space velocity: 0.12 $kg_{acetaldehyde}l_{cat.}^{-1}h^{-1}$). With quantitative acetaldehyde conversion, the selectivity for the Hünig base was 79.9 mol %.

After 68 days, the feed was changed over to 229.5 g of diisopropylamine, 98 g of acetaldehyde (molar ratio of amine/aldehyde=1.0) and 153 g of ethanol as solvent per hour (space velocity: 0.12 $kg_{acetaldehyde}l_{cat.}^{-1}h^{-1}$). With quantitative acetaldehyde conversion, the selectivity for the Hünig base was 81.3 mol %.

After 82 days, the feed was changed over to 286.9 g of diisopropylamine, 123 g of acetaldehyde (molar ratio of amine/aldehyde=1.0) and 191.2 g of ethanol as solvent per hour (space velocity: 0.15 $kg_{acetaldehyde}l_{cat.}^{-1}h^{-1}$). With quantitative acetaldehyde conversion, the selectivity for the Hünig base was 77.3 mol %.

Example 8

In a similar manner to Example 6, at 120° C., 180.5 g of diisopropylamine and 50 g of acetaldehyde (molar ratio of amine/aldehyde=1.6) were passed over the catalyst per hour in the bottom-phase procedure (space velocity: 0.06 $kg_{acetaldehyde}l_{cat.}^{-1}h^{-1}$). The amount recycled was 3 l h$^{-1}$. With quantitative acetaldehyde conversion, the selectivity for the Hünig base was 71.7 mol %.

After 5 days, the feed was changed over to 270.8 g of diisopropylamine and 75 g of acetaldehyde (molar ratio of amine/aldehyde=1.6) per hour (space velocity: 0.09 $kg_{acetaldehyde}l_{cat.}^{-1}h^{-1}$). With quantitative acetaldehyde conversion, the selectivity for the Hünig base was 72.5 mol %.

After 8 days, the feed was changed over to 361 g of diisopropylamine and 100 g of acetaldehyde (molar ratio of amine/aldehyde=1.6) per hour (space velocity: 0.13 $kg_{acetaldehyde}l_{cat.}^{-1}h^{-1}$). With quantitative acetaldehyde conversion, the selectivity for the Hünig base was 71.1 mol %.

After 12 days, the feed was changed over to 361 g of diisopropylamine and 50 g of acetaldehyde (molar ratio of amine/aldehyde=3.1) per hour (space velocity: 0.06 $kg_{acetaldehyde}l_{cat.}^{-1}h^{-1}$). With quantitative acetaldehyde conversion, the selectivity for the Hünig base was 90.0 mol %.

After 14 days, the feed was changed over to 722 g of diisopropylamine and 100 g of acetaldehyde (molar ratio of amine/aldehyde=3.0) per hour (space velocity: 0.13 $kg_{acetaldehyde}l_{cat.}^{-1}h^{-1}$). With quantitative acetaldehyde conversion, the selectivity for the Hünig base was 74.6 mol %.

After 15 days, the feed was changed over to 541.5 g of diisopropylamine and 150 g of acetaldehyde (molar ratio of amine/aldehyde=1.6) per hour (space velocity: 0.19 $kg_{acetaldehyde}l_{cat.}^{-1}h^{-1}$). With quantitative acetaldehyde conversion, the selectivity for the Hünig base was 66.1 mol %.

Example 9

Into an electrically heated tube reactor were installed 800 ml of a catalyst which consisted of 0.5% of Ru on γ-Al$_2$O$_3$ in rod form. The catalyst was reduced at atmospheric pressure at 150° C. At 100° C. and 200 bar hydrogen pressure, 181 g of diisopropylamine and 50 g of acetaldehyde (molar ratio amine/aldehyde=1.6) were passed over the catalyst (space velocity: 0.06 $kg_{acetaldehyde}l_{cat.}^{-1}h^{-1}$) per hour in the bottom-phase procedure. The amount recycled was 3 l h$^{-1}$. With quantitative acetaldehyde conversion, the selectivity for the Hünig base was 41.1 mol %.

Example 10

In a similar manner to Example 6, at 120° C. and 200 bar hydrogen pressure, 361 g of diisopropylamine and 100 g of acetaldehyde (molar ratio of amine/aldehyde=1.6) were passed over the catalyst in the trickling procedure per hour (space velocity: 0.13 $kg_{acetaldehyde}l_{cat.}^{-1}h^{-1}$). The amount recycled was 6 l h$^{-1}$. With quantitative acetaldehyde conversion, the selectivity for the Hünig base was 83.3 mol %.

After 12 days, the feed was changed over to 361 g of diisopropylamine and 50 g of acetaldehyde per hour (molar ratio of amine/aldehyde=3.1; catalyst space velocity: 0.06 $kg_{acetaldehyde}l_{cat.}^{-1}h^{-1}$). At the same time, the temperature was decreased to 110° C. with quantitative acetaldehyde conversion, the selectivity for the Hünig base was 87 mol %.

Example 11

Into an electrically heated tube reactor were installed 800 ml of a catalyst which consisted of 0.5% of Pd on ZrO$_2$ in pellet form. The catalyst was reduced at atmospheric pressure at 140° C. At 160° C. and 200 bar hydrogen pressure, 180.5 g of diisopropylamine and 50 g of acetaldehyde (molar ratio amine/aldehyde=1.6) were passed over the catalyst (space velocity: 0.06 $kg_{acetaldehyde}l_{cat.}^{-1}h^{-1}$) per hour in the bottom-phase procedure. The amount recycled was 6 l h$^{-1}$. With quantitative acetaldehyde conversion, the selectivity for the Hünig-base was 83.7 mol %.

We claim:

1. A process for preparing N-ethyldiisopropylamine by reacting acetaldehyde with diisopropylamine and hydrogen at elevated temperature and under pressure in the presence of a hydrogenation catalyst comprising an oxidic support material selected from the group consisting of zirconium dioxide, titanium dioxide, aluminum oxide, silicon dioxide, zinc oxide, magnesium oxide, cerium dioxide, clays and zeolites or mixtures thereof.

2. A process as claimed in claim 1, wherein the catalytically active mass of the catalyst comprises from 50 to 99.9% by weight of ZrO$_2$, TiO$_2$, Al$_2$O$_3$, SiO$_2$ and/or MgO and from 0.1 to 50% by weight of Cr, Mo, W, Re, Ru, Rh, Pd, Os, Ir, Pt, Ag, Au, Fe, Co, Ni and/or Cu, calculated as metals in the oxidation state 0.

3. A process as claimed in claim 1, wherein the catalytically active mass of the catalyst comprises from 60 to 99.9% by weight of ZrO$_2$.

4. A process as claimed in claim 1, wherein the reaction is carried out in the presence of excess diisopropylamine.

5. A process as claimed in claim 1, wherein unreacted diisopropylamine is recycled back to the synthesis.

6. A process as claimed in claim 1, wherein the reaction is carried out continuously in a fixed-bed reactor with liquid recirculation.

7. A process as claimed in claim 1, wherein the reaction is carried out in the presence of an inert solvent.

8. A process as claimed in claim 1, wherein the reaction is carried out at from 80 to 250° C.

9. A process as claimed in claim 1, wherein the reaction is carried out at pressures from 5 to 350 bar.

* * * * *